United States Patent [19]

Armbruster

[11] Patent Number: 4,555,245
[45] Date of Patent: Nov. 26, 1985

[54] UNDERGARMENT WITH ATTACHED ABSORBENT LINER

[75] Inventor: Thomas L. Armbruster, Norfolk, Nebr.

[73] Assignee: Comm Stitch, Norfolk, Nebr.

[21] Appl. No.: 522,813

[22] Filed: Aug. 12, 1983

[51] Int. Cl.⁴ .............................................. A61F 13/16
[52] U.S. Cl. ........................................ 604/396; 2/403
[58] Field of Search ............... 604/396, 397, 394, 385, 604/393; 2/403, 404, 405

[56] References Cited

U.S. PATENT DOCUMENTS

| 876,173 | 1/1908 | Guttman . | |
|---|---|---|---|
| 2,495,863 | 1/1950 | Paige . | |
| 2,629,380 | 2/1953 | Schweikert . | |
| 2,678,648 | 5/1954 | De Woskin . | |
| 2,842,129 | 7/1958 | Ernstorff . | |
| 3,025,856 | 3/1962 | Burwell et al. | 604/394 |
| 3,043,307 | 7/1962 | Weston . | |
| 3,237,625 | 3/1966 | Johnson . | |
| 3,368,563 | 2/1968 | Scheier . | |
| 3,496,576 | 2/1970 | Artzt . | |
| 3,599,640 | 8/1971 | Larson | 604/397 |
| 3,613,687 | 10/1971 | Kennedy | 604/396 |
| 3,636,953 | 1/1972 | Benevento . | |
| 3,648,699 | 3/1972 | Anderson et al. . | |
| 3,714,946 | 2/1973 | Rudes | 604/394 |
| 3,720,212 | 3/1973 | Kaupin . | |
| 4,114,621 | 9/1978 | Mims, Jr. . | |
| 4,145,763 | 3/1979 | Abrams et al. . | |
| 4,227,531 | 10/1980 | McLeod | 604/396 |
| 4,324,245 | 4/1982 | Mesek et al. | 604/385 |
| 4,337,771 | 7/1982 | Pieniak et al. | 604/385 |

Primary Examiner—John D. Yasko
Attorney, Agent, or Firm—Allegretti, Newitt, Witcoff & McAndrews, Ltd.

[57] ABSTRACT

An undergarment adapted for controlling moisture leakage caused by adult partial incontinence. The undergarment having a permanently attached absorbent liner that fits snugly against the undergarment wearer's body.

3 Claims, 3 Drawing Figures

UNDERGARMENT WITH ATTACHED ABSORBENT LINER

BACKGROUND OF THE INVENTION

This invention relates to an undergarment incorporating a permanently attached absorbent liner designed to prevent moisture leakage through a person's outer clothing due to adult partial incontinence.

Nearly twenty million Americans today suffer from a condition known as adult partial incontinence, also known as bladder weep. As a result of this condition, many people are forced to suffer with the discomfort and embarrassment caused by moisture penetrating undergarments and staining one's outer clothing.

The need, therefore, exists for an undergarment which will provide a means of absorbing the excess moisture caused by bladder weep, prevent seepage of that moisture through the undergarment to the outer clothing, and provide this protection in an economic and comfortable way.

One of the most common means of dealing with adult partial incontinence is through the use of adult disposable diapers. These adult disposable diapers, however, suffer from some disadvantages. The disposable diaper iks ordinarily worn in addition to an individual's standard undergarment. Wearing a combination of a disposable diaper and a cloth undergarment under one's clothing is bulky and inhibits circulation of air under one's clothing. Consequently, individuals who wear adult disposable diapers are usually hot and uncomfortable while wearing them. Further, disposable diapers cost up to $0.25 apiece and more. A partially incontinent individual using several disposable diapers a day could expect to spend hundred of dollars a year for this type of protection.

SUMMARY OF THE INVENTION

The present invention is an undergarment designed to absorb excess moisture resulting from partial incontinence in order to prevent that moisture from penetrating an individual's outer clohting. The undergarment of the present invention comprises an exterior cloth portion and an interior permanently attached absorbent liner portion. The absorbent liner portion possesses at least two layers of different material and two contoured elastic borders. One layer of the absorbent liner is made from a waterproof material and the other layer is composed of a moisture absorbent material. In the case of a two layer absorbent liner, the surface of the moisture absorbent layer contacts the skin of the undergarment wearer. The waterproof layer of the absorbent liner is situated between the absorbent layer and the inside surface of the undergarment's exterior cloth portion. Contoured elastic borders are located along the edges of the absorbent liner. These contoured elastic borders permit the absorbent liner to fit snugly against the undergarment wearer's body.

Thus, an object of this invention is to overcome the discomfort and expense associated with the prior art and provide a reusable undergarment that absorbs excess moisture produced by adult partial incontinence and prevents that moisture from penetrating the wearer's outer clothing.

Another object of this invention is to provide a reusable undergarment with an absorbent liner that fits snugly against the undergarment wearer's body.

A further object of this invention is to provide an undergarment with a permanently attached absorbent liner that is highly absorbent, stain resistant, and washable.

BRIEF DESCRIPTION OF THE DRAWINGS

In the accompanying drawings that constitute part of this specification, one embodiment of the present invention, the preferred embodiment, is depicted, and specifically

THE DETAILED DESCRIPTION OF THE PREFERRED EMBODIMENT

Figure 1:
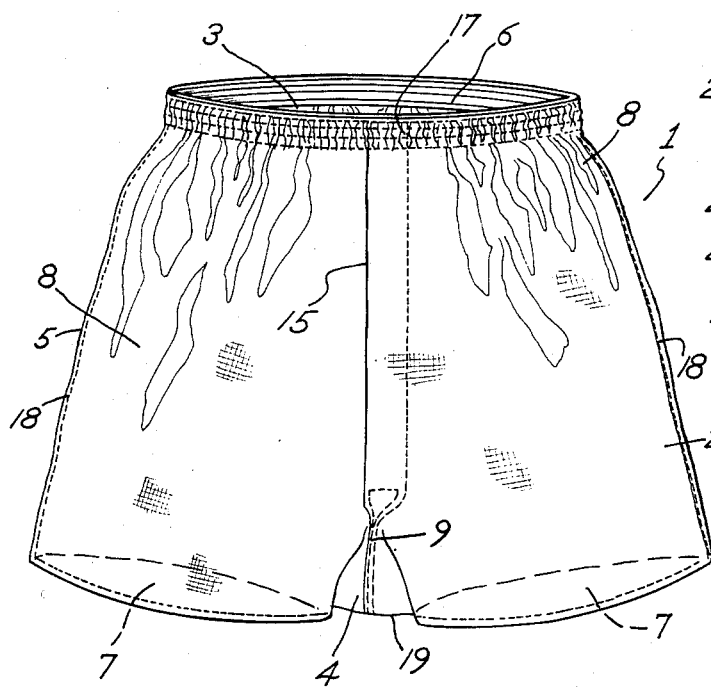
FIG. 1 is a front view of the preferred embodiment of the present invention.
Figure 3:
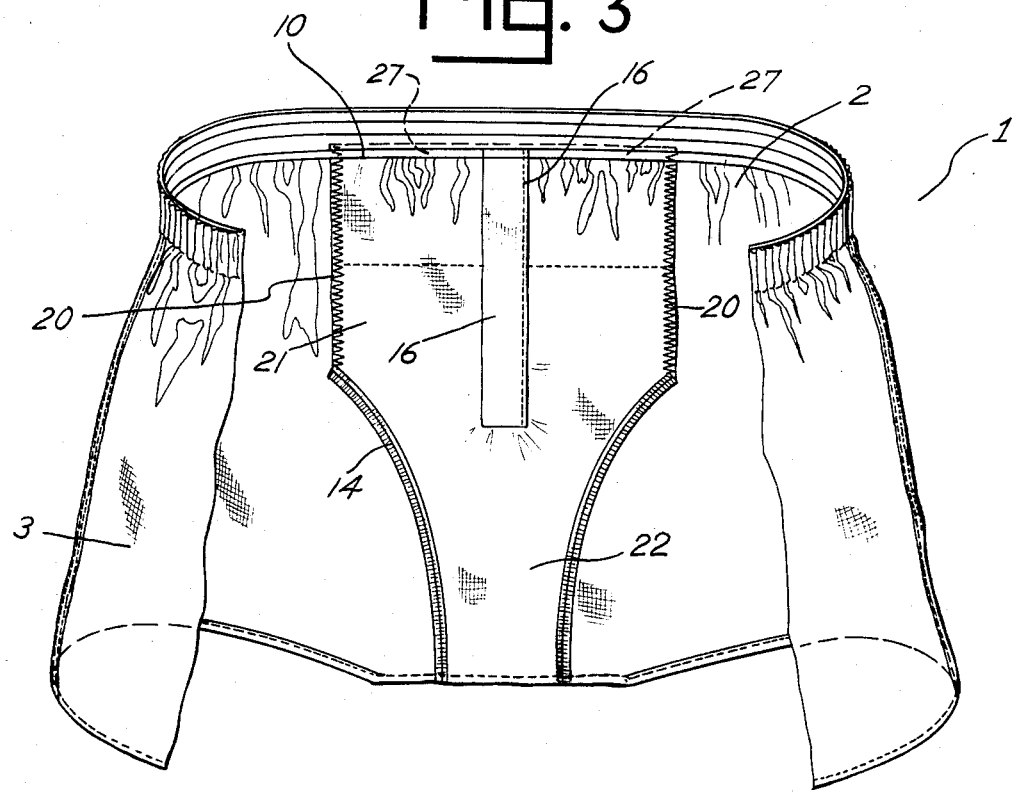
FIG. 3 is a cut-away view of the preferred embodiment of the present invention, a part of the rear panel removed, exposing the preferred embodiment of the absorbent liner in place.

Referring to FIGS. 1 and 3, the preferred embodiment of the present invention is an undergarment 1 incorporating a permanently attached absorbent liner 10. The preferred undergarment 1 includes an exterior cloth portion 5 and an interior permanently attached absorbent liner portion 10. The absorbent liner portion 10 has at least two layers of different material and two contoured elastic borders 14. One layer of the absorbent liner portion 10 is a waterproof layer 11. The second layer of the absorbent liner portion 10 is a moisture absorbent layer 12. The moisture absorbent layer 12 is disposed between the waterproof layer 11 and the skin surface of the undergarment wearer. The contoured elastic borders 14 are located along opposing edges 20 of the absorbent liner 10. The contoured elastic borders 14 of the absorbent liner 10 provide a snug fit of the absorbent liner to the body of the undergarment wearer.

The exterior cloth portion 5 of the undergarment 1 preferably comprises a front panel 2 and a rear panel 3. The front panel 2 and the rear panel 3 of the exterior cloth portion 5 are joined together so as to define a crotch section 4 extending centrally between the front and rear panels. The front panel 2, the rear panel 3, and the crotch section 4 when joined together define a waist opening 6, and two leg openings 7 at opposite sides of the crotch section 4. The permanently attached absorbent liner 10 is preferably attached to the front panel 2 and to the crotch section 4.

In the most preferred embodiment of the undergarment 1, the exterior cloth portion 5 comprises a rear panel 3 and a front panel 2 where the front panel consists of two separate front panel sections 8. The front panel sections 8 are joined together so as to form an openable fly 15 which has overlapping fly panels 16. The rear panel 3 joined to the two front panel sections 8 of the front panel 2 define the crotch section 4. The interior permanently attached absorbent liner portion 10 most preferably has two opposing edges 20, a wide area 21 flanking each side of the openable fly 15, and a narrower area 22 that overlaps the crotch section 4.

Figure 2:
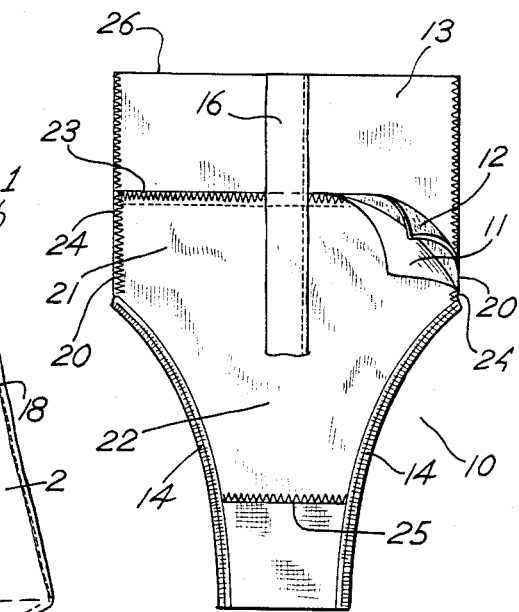
FIG. 2 is a front view of the preferred embodiment of the absorbent liner of the present invention.

Referring to FIG. 2, the most preferred embodiment of the permanently attached absorbent liner 10 is depicted. The absorbent liner 10 most preferably possesses a waterproof layer 11, a moisture absorbent layer 12, a backing layer 13, and a contoured elastic border 14 located on each of the opposing edges 20 of the absorbent liner. The waterproof layer 11, the moisture absorbent layer 12, and the backing layer 13 are located on both sides of the openable fly. Further, portions of the waterproof layer 11, the moisture absorbent layer 12, and the backing layer 13 preferably extend into the overlapping fly panels 16.

The exterior cloth portion 5 is most preferably made from a cloth comprising fifty percent cotton fiber and fifty percent polyester fiber. The waterproof layer 11 is preferably made from neoprene. The waterproof layer 11 separates the absorbent layer 12 from the two front panel sections 8 and the crotch section 4 of the exterior cloth portion 5. The waterproof layer 11, therefore, serves to prevent moisture present in the absorbent layer 12 from penetrating the exterior cloth portion 5 of the undergarment 1 and soiling the outer clothing of the undergarment wearer. The absorbent layer 12 is preferably made from one hundred percent cotton fibers. The absorbent layer 12 separates the waterproof layer 11 from the backing layer 13. The absorbent layer 12 is designed to absorb and retain moisture produced by bladder weep. The backing layer 13 is preferably made from one hundred percent nylon fiber. The backing layer 13 separates the absorbent layer 12 from the skin of the undergarment wearer. The backing layer 13 draws moisture away from the wearer and into the absorbent layer 12 for retention.

The permanently attached absorbent liner 10 most preferably has a narrow area 22 and a wide area 21. Contoured elastic borders 14 are most preferably located along the edges 20 of the absorbent liner in the narrow area 22. These contoured elastic borders 14 serve to provide a snug fit for the absorbent liner 10 to the body of the undergarment wearer. Further, the snug fit of the absorbent liner to the wearer provided by the contoured elastic borders 14 prevents moisture from escaping down the leg of the undergarment wearer rather than being retained by the moisture absorbent layer 12 of the liner 10.

To construct the preferred embodiment of the exterior cloth portion 5 of the preferred embodiment for undergarment 1, the two front panel sections 8 of the front panel 12 are joined along front panel seam 9 and at waistband seam 17 near the waist opening 6. Between the waistband seam 17 and seam 9 that join the front panel sections 8 is the openable fly 15 and the overlapping fly panels 16. The assembled front panel sections are thereafter joined to the rear panel 3 along side seams 18 and at the crotch section seam 19.

The preferred embodiment of the interior permanently attached absorbent liner 10 of the present invention is constructed from three different layers of material, the waterproof layer 11, the moisture absorbent layer 12, and the backing layer 13. The waterproof layer 11 and the moisture absorbent layer 12 are joined to the backing layer 13 along three seams, the liner top seam 23, and the liner side seams 24 which extend along the absorbent liner edges 20 through the narrow area 22 and underneath the contoured elastic borders 14. Most preferably the absorbent layer 12 and the waterproof layer 11 are joined to each other at a bottom seam 25, but this bottom seam does not join the backing layer 13. The benefit of not joining the bottom seam 25 to the backing layer 13 is that air may then travel more easily between the absorbent layer 12 and the backing layer 13, thereby facilitating air drying and evaporation of the moisture trapped by the absorbent layer of the liner.

The absorbent liner construction of the preferred embodiment is then attached to the inside surface of the exterior cloth portion 5 at three points. The bottom of the absorbent liner 10 is joined to the exterior cloth portion 5 along crotch section seam 19. The edges 20 of the absorbent liner are joined to the exterior cloth portion 5 along liner side seams 24. The top edge 26 of the absorbent liner 10 is connected to the front panel 2 of the exterior cloth portion 5 at seams 27 near the waist opening 6.

While in the foregoing, there has been provided a detailed description of particular embodiments of the present invention, it is to be understood that equivalents are to be included within the scope of the invention as claimed.

What is claimed is:

1. An undergarment comprising an exterior cloth portion and an interior permanently attached absorbent liner portion; the exterior cloth portion having a waist opening, two leg openings that have a circumference greater than that of a wearer's leg so that the openings fit loosely about the leg, and an openable fly; the absorbent liner portion having a wide area disposed about the openable fly, at least two layers and two contoured elastic borders, one layer being waterproof and the other layer being moisture absorbent and disposed between the waterproof layer and the undergarment wearer, each contoured elastic border forming an edge on the absorbent liner so that the absorbent liner fits snugly against the undergarment wearer's body.

2. An undergarment comprising a front panel, a rear panel, and an absorbent liner; the front panel and the rear panel being joined at a crotch section extending centrally between the front and rear panels, the front panel having an openable fly, the front panel, the rear panel, and the crotch section cooperating to form a waist opening and two leg openings at opposite sides of the crotch section that have a circumference greater than that of a wearer's leg so that the openings fit loosely about the leg; the absorbent liner having a wide area disposed about the openable fly being permanently attached to the front panel and having a narrower area overlapping and permanently attached to the crotch section and having at least two layers, a waterproof layer and an absorbent layer, the absorbent liner having two contoured elastic borders adapted to fit the absorbent liner snugly against a person wearing the garment.

3. A man's undergarment comprising an exterior cloth portion and an interior permanently attached absorbent liner portion; the exterior cloth portion having a rear panel and a front panel, the front panel having two front panel sections joined together to form an openable fly having overlapping fly panels, and a crotch section, the rear panel joined to the two front panel sections and the crotch section forming a waist opening and two leg openings at opposite sides of the crotch section; the interior permanently attached absorbent liner portion having two opposing edges, a wide area disposed about the openable fly, and a narrower area overlapping the crotch section, the absorbent liner comprising a waterproof layer, an absorbent layer, a backing layer, and a contoured elastic border on each of the opposing edges of the absorbent liner; the waterproof layer, the absorbent layer, and the backing layer being disposed on both sides of the openable fly and extending into the overlapping fly panels, the waterproof layer disposed between the absorbent layer and the two front panel sections and the crotch section of the exterior cloth portion, the waterproof layer thereby being adapted to prevent moisture in the absorbent layer from penetrating the exterior cloth portion; the absorbent layer being disposed between the backing layer and the waterproof layer, the absorbent layer thereby being adapted to absorb moisture produced by bladder weep; the backing layer being disposed between the absorbent layer and the body of the undergarment wearer, the backing layer thereby being adapted to draw moisture away from the wearer and into the absorbent layer; the absorbent liner narrowing in width toward the crotch section, the contoured elastic borders being disposed on each edge of the absorbent liner along the narrower area overlapping the crotch section, the contoured elastic borders being adapted to provide a snug fit of the absorbent liner to the wearer and thereby being adapted to prevent moisture from escaping the absorbent liner.

* * * * *